(12) United States Patent
Barnes et al.

(10) Patent No.: US 6,676,602 B1
(45) Date of Patent: Jan. 13, 2004

(54) TWO DIMENSIONAL ARRAY SWITCHING FOR BEAMFORMING IN A VOLUME

(75) Inventors: Stephen R. Barnes, Bellevue, WA (US); Todor Sheljaskow, Issaquah, WA (US); Robert N. Phelps, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/202,922

(22) Filed: Jul. 25, 2002

(51) Int. Cl.$^7$ ................................................ A61B 8/00
(52) U.S. Cl. ............................................... 600/443
(58) Field of Search .................... 73/626; 600/447, 600/443, 448, 449, 455, 456

(56) References Cited

U.S. PATENT DOCUMENTS

| | | | |
|---|---|---|---|
| 5,563,346 A | | 10/1996 | Bartelt et al. |
| 6,126,602 A | * | 10/2000 | Savord et al. ............. 600/447 |
| 6,128,958 A | * | 10/2000 | Cain .......................... 73/626 |
| 6,238,346 B1 | | 5/2001 | Mason |
| 6,279,399 B1 | | 8/2001 | Holm |

* cited by examiner

*Primary Examiner*—Francis J. Jaworski
*Assistant Examiner*—Maulin Patel (57) ABSTRACT

Methods and systems for electronically scanning within a three dimensional volume while minimizing the number of system channels and associated cables connecting a two-dimensional array of elements to an ultrasound system are provided. An array of semiconductor or micro-machined switches electronically interconnect various elements of the two-dimensional array. Elements associated with a substantially same time delay are connected together as a macro element, reducing the number of independent elements to be connected to beamforming or system channels. To beam form in the desired direction, the macro elements are configured as a phased array or along substantially straight lines in at least two dimensions (i.e. along the face of the two-dimensional transducer). Such macro elements allow transmission and reception along beams that are at an angle other than normal to the two-dimensional transducer array. Beams at such angles may be used to acquire information beyond the azimuth and elevation extent of the two-dimensional array. Various configurations of macro elements are possible. For example, the macro elements in each configuration are parallel across the two-dimensional array, but different configurations are associated with rotation of the macro elements such that each configuration is at a different angle on the two-dimensional array. As another example, the macro elements are configured in a plurality of separate rows of parallel macro elements (i.e. configured as a 1.25D, 1.5D or 1.75D array of macro elements). Two or more switches are provided for each system channel, allowing for rotation of macro. elements. The different rotation positions of macro elements defines different two-dimensional scan planes within the three-dimensional volume. Two, three or more switches are provided for each element to interconnect the elements in many possible combinations.

39 Claims, 6 Drawing Sheets

FIG. 1
SERIES CONNECTION

FIG. 2
PARALLEL CONNECTION

TWO DIMENSIONAL ARRAY SWITCHING FOR BEAMFORMING IN A VOLUME

BACKGROUND

This present invention relates to three-dimensional imaging. In particular, the present invention relates to scanning a three-dimensional volume with a two-dimensional array of acoustic transducer elements.

Typical aperture sizes for two-dimensional diagnostic ultrasound transducers range anywhere from 30 wavelengths by 30 wavelengths up to 30 wavelengths by 200 wavelengths. For example, a two-dimensional array has on the order of 60 by 60 to 60 by 200 spatial sampling locations or elements. Such two-dimensional arrays have from 4,000 to 12,000 elements.

Typical high performance medical diagnostic ultrasound systems have about 200 beamforming channels and an associated 200 signal conductors in the transducer cable connecting the beamforming channels to the transducer array. Currently, 4,000 transmission lines are not provided in a clinically useful cable. Current ultrasound systems and transducers may not be capable of real-time electronic, fully sampled three-dimensional beamformation without significantly sacrificing image quality or clinical usefulness.

An alternate approach to three-dimensional imaging uses beamforming electronics within the transducer to avoid a large number of transmission lines in the cable or a large number of beamforming channels in the system. However, the circuitry located in the transducer has a high degree of complexity in terms of both the number of circuit functions, number of components and cost.

Another approach uses a sparse array for three-dimensional imaging to reduce the number of transmission lines used in a cable. U.S. Pat. No. 6,279,399 uses a combination of a sparse array for three-dimensional imaging and a configuration of elements for two-dimensional imaging. A set of mode switches or multiplexers configure the transducer elements to form either a one-dimensional array providing a two-dimensional scan mode or a two-dimensional sparse array providing a three-dimensional scan mode. In the two-dimensional scan mode, the length of the sparse elements is extended in one direction, forming a conventional one-dimensional array for two-dimensional images in a single fixed image plane. However, sparse arrays for three dimensional imaging have poor sensitivity and contrast resolution.

In U.S. Pat. No. 5,563,346, three-dimensional scanning is provided using a minimum number of signal lines. A two-dimensional array operates as a linear, annular array to form beams normal to the array surface at different locations on the two-dimensional array. Concentric rings of elements are interconnected using a multiplexer or switching. Each concentric ring represents common delay areas for beamforming, so connects with a single signal line. However, the normal beam constraint limits the volume which can be scanned by the aperture size and shape of the two-dimensional array.

BRIEF SUMMARY

The present invention is defined by the following claims, and nothing in this section should be taken as a limitation on those claims. By way of introduction, the preferred embodiments described below include methods and systems for electronically scanning within a three dimensional volume while minimizing the number of system channels and associated cables connecting a two-dimensional array of elements to an ultrasound system.

An array of semiconductor or micro-machined switches electronically interconnects various elements of the two-dimensional array. Elements associated with a substantially same time delay are connected together as a macro element, reducing the number of elements to be connected to beamforming or system channels. To beam form in the desired direction, the macro elements are configured as a phased array or along substantially straight lines in at least two dimensions (i.e. along the face of the two-dimensional transducer). Such macro elements allow transmission and reception along beams that are at an angle other than normal to the two-dimensional transducer array. Beams at such angles may be used to acquire information beyond the azimuth and elevation extent of the two-dimensional array.

Various configurations of macro elements are possible. For example, the macro elements in each configuration are parallel across the two-dimensional array, but different configurations are associated with rotation of the macro elements such that each configuration is at a different angle on the two-dimensional array. As another example, the macro elements are configured in a plurality of separate rows of parallel macro elements (i.e. configured as a 1.5D or 1.75D array of macro elements). As used herein, a 1.25D array includes arrays using a center row of elements short in the elevation extent for close focal regions and longer in elevation extent for farther focal regions, 1.5D array includes three or more rows of elements where the outside rows in opposing side pairs are each connected to the same beamformer channels and 1.75D includes independent operation of a plurality of rows of elements.

In one embodiment, two or more switches are provided for each system channel, allowing for rotation of macro elements. The different rotation positions of macro elements defines different two-dimensional scan planes within the three-dimensional volume. Two, three or more switches are provided for each element to interconnect the elements in many possible combinations.

Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views. Angular directions given in the specification are referenced counter-clockwise from 0° (pointing horizontally to the right).

DETAILED DESCRIPTION OF THE PREFERRED EMBODIMENTS

Electronically steered three-dimensional imaging is provided with a minimum of system channels and associated cables. Existing ultrasound systems with one hundred and twenty eight, two hundred or other numbers of system channels may be used without requiring more system channels or more signal conductors in the transducer cable. Both linear array and phased array beamforming may be implemented.

In general, beamforming involves the superposition in time of signals traveling between substantially one point in space on the object under study and diverse multiple spatial locations or elements on the transducer. Transmit beamforming designates transit from many elements of an array to a focal point, whereas receive beamforming designates transit from the focal point to the many elements. In the case of transmit beamforming, the signals sent from the various elements are delayed relative to one another, with signals to travel a shorter distance being sent out later in time. Superposition occurs as the signals simultaneously converge at the focal point. In the case of receive beamforming, the signals received at the elements are electronically delayed relative to one another to superpose information representing the focal point. In either case, the relative delays required for superposition in time are derived to compensate for the relative propagation times along the diverse paths to or from the focal point. Concentric spherical shells centered on the focal point define spatial locations of a same or constant propagation time to or from the focal point.

The beamforming delays are defined by the intersection of these concentric spherical isochronal-shells and the surface of the array. Constant time delay contours are thus continuous across the face of the array or extend across adjacent elements of a two dimensional array. Array elements intersected by the same contour use substantially the same beamforming delay.

In linear array beamforming, the beams are normal to the face of the array. For a flat array, the loci of constant delay contours for any point in the beam are annular rings centered on the intersection of the beam and the array surface. The center point for the rings is stationary during the beamforming process for all points along the beam at that beam location. Multi-dimensional imaging is accomplished by moving the location of the beams across the array surface, moving the location of the annular ring loci of constant delay contours between beams.

For linear array beamforming with a curvilinear array, the constant delay contours are distorted somewhat from a set of annular rings to a set of ellipsoidal rings. The ratio of the elliptic radii are range dependent. The geometry of the curvilinear array may provide constant time delay contours that are annular rings and are independent of range if the curvilinear geometry is such that the effective surface of the array is spherical.

An electronically configurable annular array is implemented using a two-dimensional array of acoustic transducer elements and an array of semiconductor or microelectromechanical system (MEMS) switches. The switches electronically connect elements together into annular ring (e.g. circle or elliptical) shaped macro elements. The beam is placed at any point on the array by changing the switch states to center the annular rings or macro elements in a new location. A three-dimensional volume can be sampled whose bounds are the normal projection of the periphery of the array.

In phased array beamforming, the beam origin is fixed, and the angle between the beam and the array is varied from beam-to-beam to achieve multi-dimensional imaging. At any focal point in space, the beamforming loci of constant time delay is a set of annular rings centered on a normal projection from the array surface to the focal point. The projection from the focal point onto the array surface is at a normal to the array surface from the focal point (i.e. the rings are centered on a normal to the array surface which passes through the focal point). Since many of the beams are angled with respect to the array surface, the projection of the focal point on the array surface constantly changes position for the dynamically focused receive generation of the beam. The loci of constant delay on the array changes shape during the receive beamforming along any angled beam. In these cases, the contours start as a set of annular rings for a focal point at the skin which translate off the edge of the array for more distant focal points and end as slightly curved or substantially straight parallel lines for the most distant focal points. For example, a beam angled at 45° to a 2.5 MHz 12 mm by 12 mm array with a fixed lens having a focal length of 70 mm results in constant delay contours that are substantially straight across the array for points along the beam between 50 mm and 120 mm.

An electronically rotated phased array may be implemented using the two-dimensional array of elements and the array of semiconductor or MEMS switches. The switches electronically connect elements into a phased array of macro elements. For focal point locations over most of the depth of the beam, the macro elements comprise a plurality of parallel, substantially straight lines. Where response time of switches within the electronically configurable array is sufficient, the interconnection of elements to correspond with the constant delay contours dynamically changes during the reception of a beam, such as changing from concentric circular, to elliptical, and to substantially straight macro elements. Where the response time of the switches is not sufficient, the macro elements may represent a contour derived from and used for multiple focal points without any dynamic changes for a given beam. Alternatively or additionally, the macro elements are grouped, such as in rows, corresponding to different focal points. Different rows or all of the rows are used for different focal points. The macro elements are aligned in an image plane direction. By reconfiguring the macro elements, the image plane direction is rotated for scanning the three-dimensional volume. A set of rotated two-dimensional image planes are acquired as a three-dimensional data set. The rotated phased array of macro elements may be either a 1D, 1.75D or other phased array.

Figure 1:
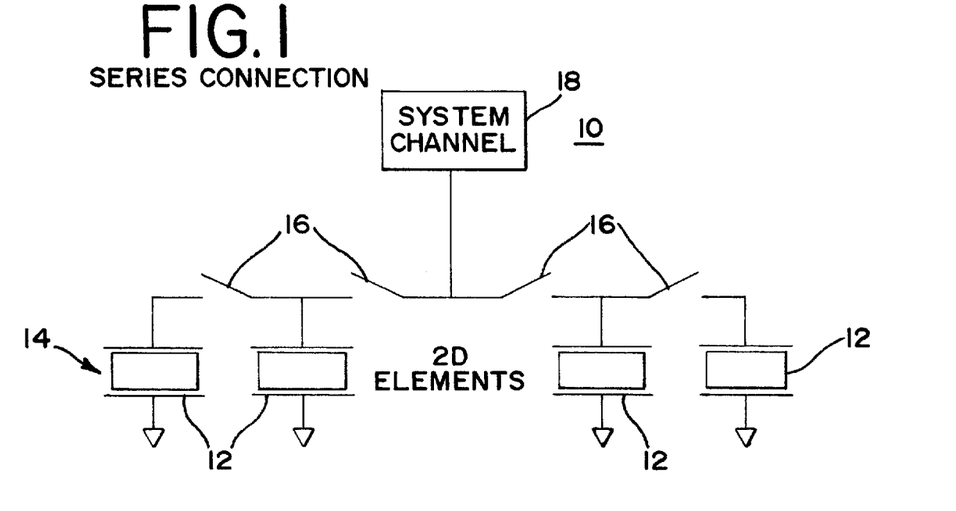
FIGS. 1 and 2 are two embodiments of systems for connecting a plurality of elements of a two-dimensional transducer array with a system channel.
Figure 2:
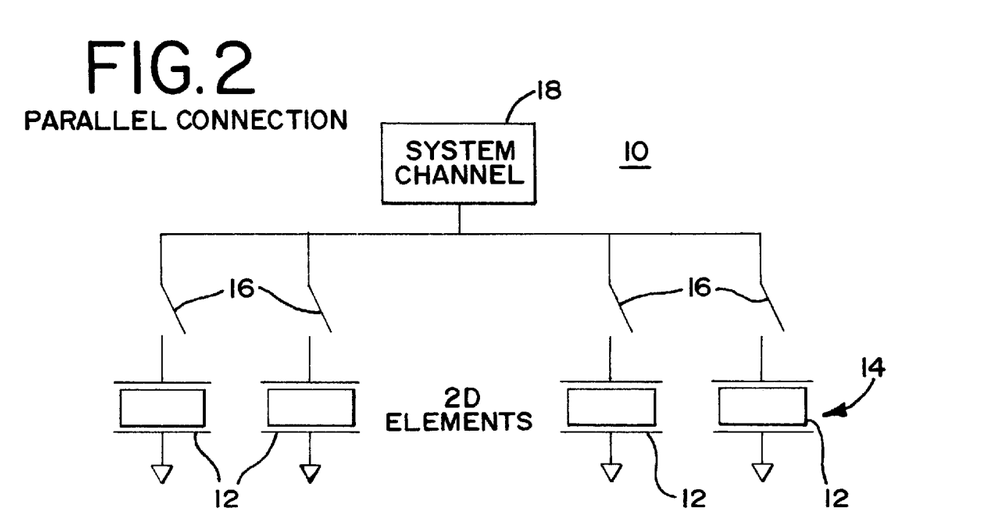

FIGS. 1 and 2 show two embodiments of two-dimensional transducer array systems 10 for ultrasonically scanning a three dimensional volume. The systems 10 comprise a plurality of acoustic transducer elements 12 of a two-dimensional array 14, a plurality of interconnectable switches 16 and a system channel 18. Additional, different and/or fewer components may be used, such as including additional switches to connect one or more of the elements with a different system channel 18.

The acoustic transducer elements 12 comprise lead zirconate titanate (PZT) piezoelectric transduction material, ferroelectric relaxor or PVDF materials, capacitive membrane ultrasonic transducer (cMUT) materials, micromachined membranes or beams, microelectromechanical devices, other piezoelectric material, or other means for acoustic to electric transduction. All of the elements comprise a same type of material, but multiple types of acoustic transducer materials may be used for different elements 12 of the array 14. The elements 12 have one of various possible shapes, such as triangular, rectangular, square, polygonal, circular, irregular or any combination of shapes on the face of the element 12 or portion of the element 12 placed adjacent a volume to be scanned.

The two-dimensional array 14 is an N by M arrangement of elements 12, where N and M are both greater than one. The area array sampling pattern or relative placement of one element 12 to another element 12 is based on any sampling method, such as a triangular grid, rectangular grid, hexagonal grid, irregular grid, or random grid. Various spacing may be provided, such as ½ or one wavelength spacing between the centers of adjacent elements. The face or surface of the entire array 14 is square, rectangular, triangular, hexagonal, irregular or other shape. Any of various possible multi-dimensional arrangements of elements 12 may be used for the two-dimensional array 14. The array 14 is either flat or includes concave or convex curvature.

The switches 16 comprise semiconductor switches, transistors, MEMS switches or other switches for electrically connecting or disconnecting elements 12 and/or system channels 18. In one embodiment, MEMS switches comprising electrically controlled deflectable membranes or beams are used. The MEMS switches are sized so that the number of switches associated with each element 12 covers substantially the area of the element 12, but other sizes may be provided. The MEMS switches are fabricated using photolithography and/or semiconductor fabrication processes allowing a large number of devices to be fabricated on a single silicon or other semiconductor chip, but two or more chips may also be used. It is also possible to include electronic circuitry and MEMS devices on the same silicon chip, allowing the switch control circuitry to be integrated with the switches 16 on the same chip. The switches 16 and array 14 may be provided in a probe housing, providing a small, low cost, high yield three-dimensional imaging transducer using low power consumption, resulting in better transducer thermal efficiency. Minimal or no changes are needed in conventional system channel hardware.

The switches 16 are operable to interconnect the elements 12 into a plurality of macro elements. Each macro element comprises at least two electrically connected elements 12. For example, the elements 12 are connected in a substantially straight line, chevron patterns or in curving patterns in at least two dimensions (i.e. across the face of the transducer array 14). For operation as a phased array, each macro element is continuous across the face of the two-dimensional array or a defined aperture, crossing from one boundary of the array of macro elements to another boundary. For example, the macro elements extend between boundaries sub-dividing a 1.75D array into rows. As another example, each curved or straight macro element extends from one edge of the two-dimensional array to another edge. In alternative embodiments, one or more macro elements extend only partially between boundaries.

The array of switches 16 allow multiple elements 12 associated with substantially the same beamforming delay to be connected as a macro element to the same system channel 18. The macro elements reduce the ratio of system channels 18 to elements 12. The ideal time delay required for a location on an element 12 in general varies across its surface. The optimal time delay for an element 12 is the average of the ideal time delays of all points on the element surface. This average is close to the time delay for the isochronal contour which bisects the element 12. For smaller elements 12, the interconnected elements 12 of each macro element more closely match the isochronal contour which bisects the elements 12. The common delay contour used for a macro element conceptually divides each element 12 into two areas. The beamforming is associated with fewer artifacts the more the two areas are the same or equal in area. In one embodiment, the delay applied by the system channel 18 is varied, such as varying a phase or delay, to account for the differences in area within or outside of the contour (i.e. the contour position is averaged based on the element 12 positioning for fine tuning the delay).

Other adjustments of the transmit or receive processes or hardware may be used based on the macro element configurations. For example, the spectrum of the transmit waveform or the receive filtering varies as a function of the number of elements 12 connected with the system channel 18. In general, a larger number of elements 12 interconnected as a macro element decreases the impedance of the macro element and configurable system impedance of system channel 18 may be changed to optimize impedance matching or to achieve the desired response.

The switches 16 are operable to connect with the system channel 18 in a series arrangement, parallel arrangement or combinations thereof. FIG. 1 shows the switches 16 in a series connection. The series connection uses the fewest switches 16, but the series switch impedance varies for the various elements 12 and accumulates to greater values for elements 12 connected farthest from the connection with the system channel 18. If the switch impedance is significant, the amplitude and possibly the frequency response of the element 12 changes as a function of the number of series switches 16 in the path to the system channel 18.

FIG. 2 shows the switches 16 in a parallel connection. In the parallel arrangement, the interconnection paths have the same switch impedance, but more switches 16 may be used than for the series arrangement. In the parallel arrangement, a multiplexing tree structure between the elements 12 and the system channel 18 (e.g. multiple layers of switches 16 between the elements 12 and the system channel 18) may be used to reduce the number of switches 16. As shown, one layer of switches 16 are provided. In one embodiment further described below, the array of switches 16 operates in two functional levels or groupings: the first functional level interconnecting elements 12 into isochronal groups or macro elements using series connections and the second functional level connecting system channels 18 to various macro elements. In alternative embodiments, other switch array divisions may be used.

More than one switch 16 is provided for each element 12. The switches 16 are operable to connect adjacent elements 12 together. FIGS. 10, 11 and 3–5 show embodiments of acoustic array sampling pattern and switch topology combinations.

Figure 10:
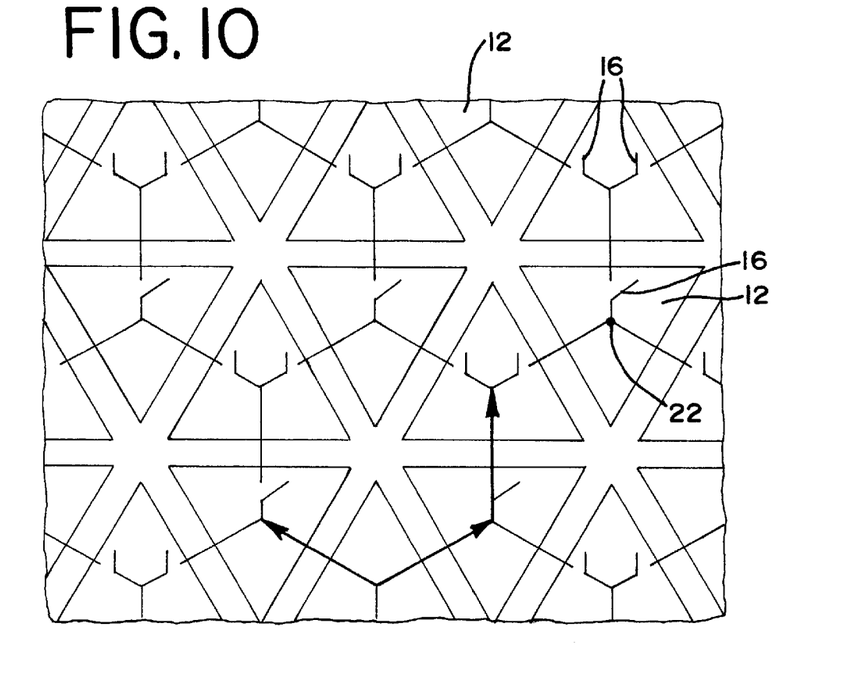

FIG. 10 shows an average of one and a half switches 16 per element 12 using the series connection topology. Every other element 12 uses two switches 16 and the other elements use one switch 16. The elements 12 are shaped and positioned in a triangular sampling grid for the two-dimensional array 14. The switches 16 between elements 12 on the triangular sampling grid allow connection of each element 12 to any of three adjacent elements 12 sharing a common edge. Nodes 22 represent connections of the switches 16 to electrodes of the elements 12. Nodes at other positions on the element 12 may be used.

Figure 11:
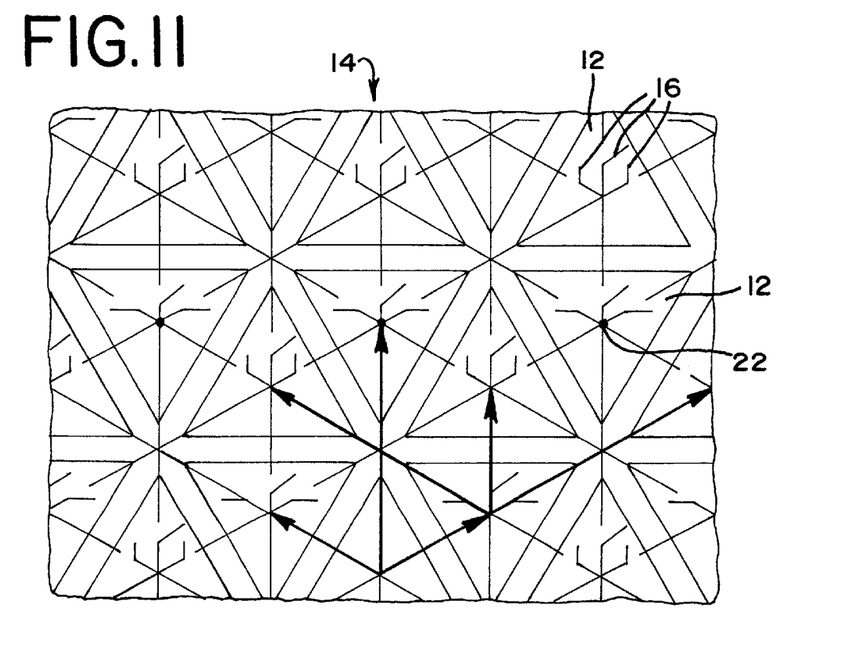

FIG. 11 shows an average of three switches 16 per element 12 using the series connection topology. The elements 12 are shaped and positioned in a triangular sampling grid for the two-dimensional array 14. The switches 16 between elements 12 on the triangular sampling grid allow connection of each element 12 to any of six adjacent elements 12 sharing a common edge or corner. Nodes 22 represent connections of the switches 16 to electrodes of the elements 12. Nodes at other positions on the element 12 may be used.

Figure 3:
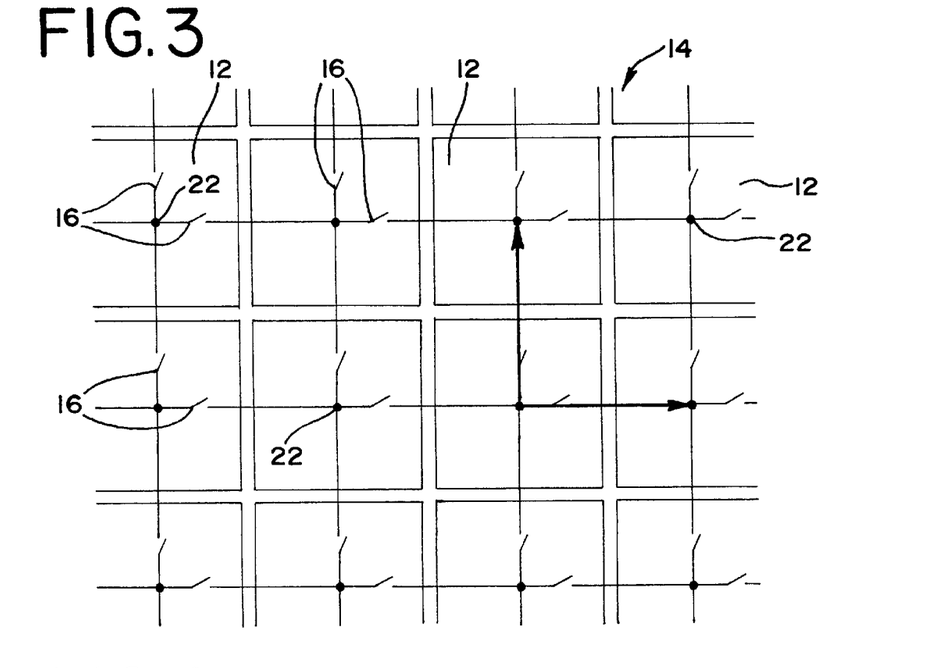
FIGS. 3–5, 10 and 11 are embodiments of switching patterns for interconnection of elements of a two-dimensional transducer array.

FIG. 3 shows two switches 16 per element 12 using the series connection topology. The elements 12 are shaped and positioned in a rectangular sampling grid for the two-dimensional array 14. Two switches 16 per element 12 on the rectangular sampling grid allows connection of each element 12 to any of two adjacent elements 12 in the 0° and 90° directions (see the axis of each bold line in FIG. 3). Alternately, the switches 16 connect in the 45° and 135° or other combination of directions. Nodes 22 represent connections of the switches 16 to electrodes of the elements 12. Nodes at other positions on the element 12 may be used.

Figure 4:
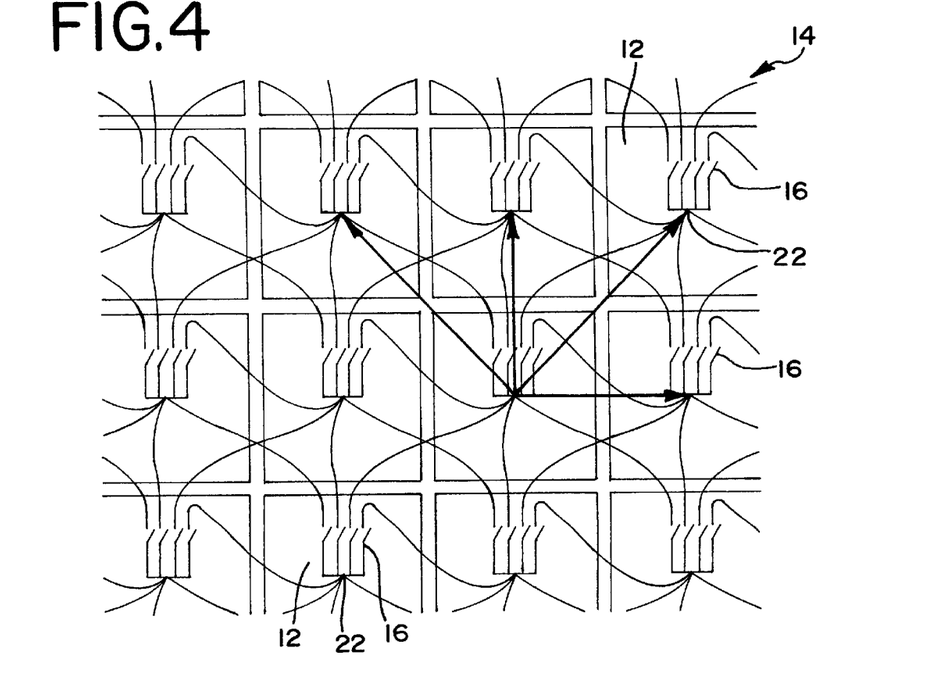

FIG. 4 shows four switches 16 per element 12 using the series connection topology. The elements 12 are shaped and positioned in a rectangular sampling grid for the two-dimensional array 14. Four switches 16 per element 12 on the rectangular sampling grid allows connection of each element 12 to any of the adjacent elements in the 0°, 45°, 90°, and 135° directions (see the axis of each bold line in FIG. 4). Alternatively, the switches 16 connect elements 12 in other angular combinations.

Figure 5:
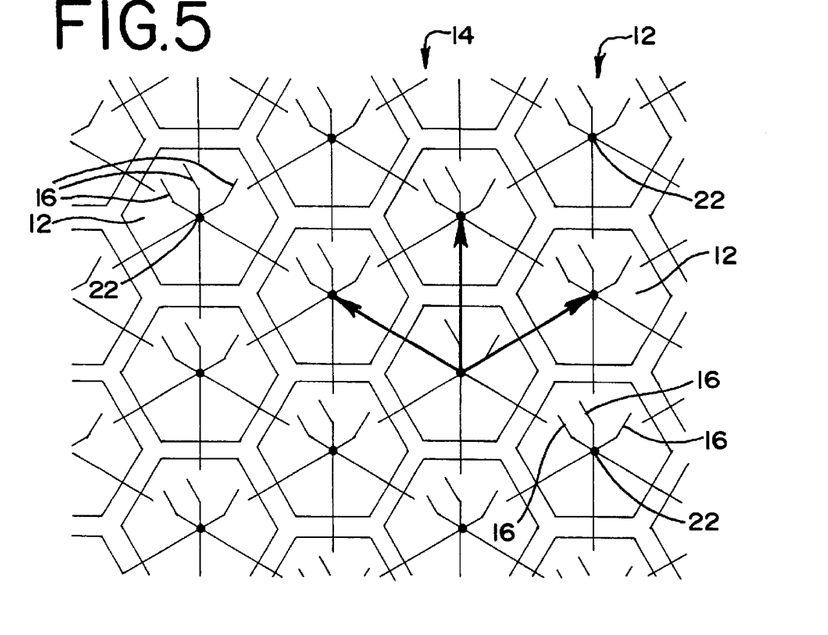

FIG. 5 shows three switches 16 per element 12 using the series connection topology. The elements 12 are shaped and positioned in a hexagonal sampling grid for the two-dimensional array 14. Three switches 16 per element 12 on the hexagonal sampling grid allows connection of each element 12 to any of the adjacent elements 12 in the 30°, 90°, and 150° directions (see the axis of each bold line in FIG. 5).

The one and a half switches 16 per element 12 with a triangular sampling grid of FIG. 10, two switches 16 per element 12 with a rectangular sampling grid of FIG. 3 and three switches 16 per element 12 with hexagonal sampling grid of FIG. 5 may avoid crossing wires or signal lines for the series connection topology as shown in FIG. 4. Avoiding wire crossings minimizes the number of wiring layers in a semiconductor chip and reduces the number of vias for MEMS switch layers by a factor of two. The choice of the number switches 16 per element 12 and the two-dimensional sampling grid geometry involves a tradeoff between the macro element directivity and effective macro element pitch. For example, a disadvantage for the two switches 16 per element 12 with the rectangular grid is a variation in pitch for the macro element. One of the maximum dimensions of a macro element extending along a 45° angle within the two-dimensional array 14 is a little over twice the two-dimensional grid pitch and the effective macro element pitch is about 1.4 times the two-dimensional array grid pitch. To achieve the similar macro element directivity and grating lobe level compared to the other configurations, the grid pitch is finer for the array of FIG. 3 than for FIG. 4.

Using the switches 16, the elements 12 interconnect to form a plurality of macro elements across the two-dimensional array 14. The macro elements are configured for beamforming along a beam line extending at a normal or a non-normal angle to the two-dimensional array 14. For example, the macro elements are configured to define a two-dimensional scan plane, such as a plurality of substantially straight, parallel macro elements. A plurality of beams are sequentially formed to scan the two-dimensional scan plane. Transmit and receive delays are provided between the macro elements to electronically steer the beams within the two-dimensional scan plane. To generate beams at different angles in the same scan plane, the same macro elements are used or the switches 16 re-interconnect the elements 12 into different macro element configurations. The different macro element configurations correspond to different common delay contours on the two-dimensional array. The angle or curvature of the macro elements corresponds to the angle of the beam to the two-dimensional array 14. For beams with focal points that extend beyond the aperture or size of the two-dimensional array 14, the macro elements become substantially straight. Accordingly, substantially straight may include some curvature. In one embodiment, the macro elements for beams with focal points that extend beyond the aperture or size of the two-dimensional array 14 extend across the face or elevation aperture of the array from one boundary (e.g. edge of the two-dimensional array or edge of a row in a 1.75D configuration) to another boundary For more normal beams or beams at small angles, the macro elements curve to form at least some hyperbolic, elliptic, or circular functions.

To scan within a different two-dimensional scan plane, the switches 16 re-interconnect the elements 12 into different macro element configurations. The macro elements of one embodiment include a plurality of substantially straight, parallel macro elements extending across the array 14 to effectively form a one dimensional array of macro elements. The different macro element configurations correspond to different angles of the parallel, straight macro elements on the two-dimensional array. For example, each macro element comprises at least two elements in a substantially straight line in at least two dimensions along a zero degree axis of the two-dimensional array. After reconfiguration, the substantially straight, parallel macro elements extend along a 3 degree axis. The different angles correspond to different two-dimensional scan planes.

A configurable 1.25D array can be implemented by changing the length of the plurality of substantially straight macro elements as a function of imaging depth. Shorter macro elements are used for shallow imaging depths and longer macro elements used for deeper depths.

Figure 9:
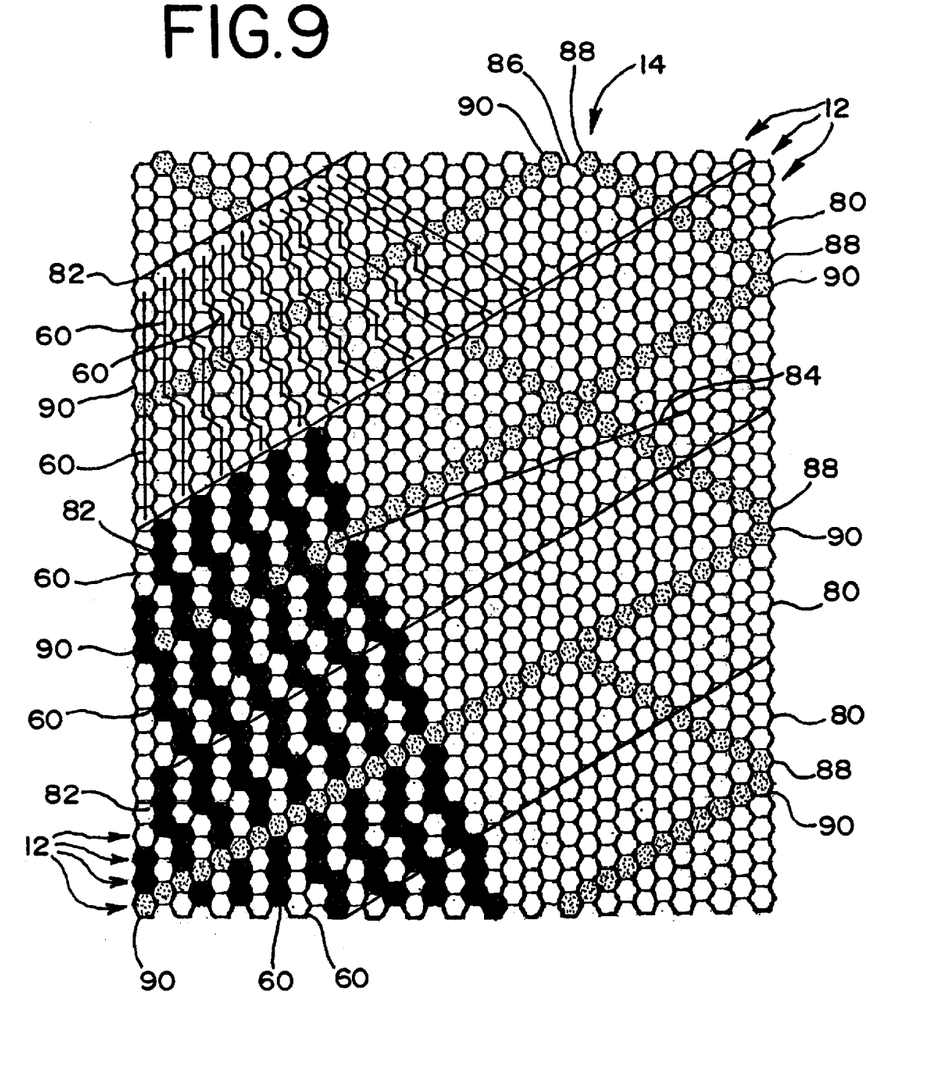

FIG. 9 shows an alternative embodiment. A plurality of macro elements are configured in at least two parallel rows. Each row comprises a plurality of substantially parallel, straight macro elements. This configuration effectively provides a 1.5D or 1.75D array of macro elements. The macro elements in this embodiment may be rotated relative to the two-dimensional array 14 for forming different two-dimensional scanning planes within the three-dimensional volume.

Each macro element is switchably connected with one of a plurality of system channels 18. Each system channel 18 comprises a receive beamformer channel, a transmit beamformer channel, a conductor connecting the macro element to a transmit or receive beamformer and/or an electrical connection to the ultrasound system separate from the electrical connection to the ultrasound system of other macro elements. For example, the system channel includes a cable connecting the array 14 to the ultrasound system, a transmit/receive switch and a selected one of a transmit and receive beamformer channel. The system channels 18 are operable to be connected with respective macro elements using switches 16 within the same housing as the array 14 or elsewhere for configuring the macro element connection to a selected system channel. Such switches 16 are in addition to the transmit/receive switch discussed above. In one embodiment, at least two switches 16 are provided for each system channel 18. By using multiple switches 16 for each system channel 18, the macro elements may be re-configured at different angles, in different rows, for different aperture lengths or other characteristics in addition to mere selection of two different array configurations.

Figure 6:
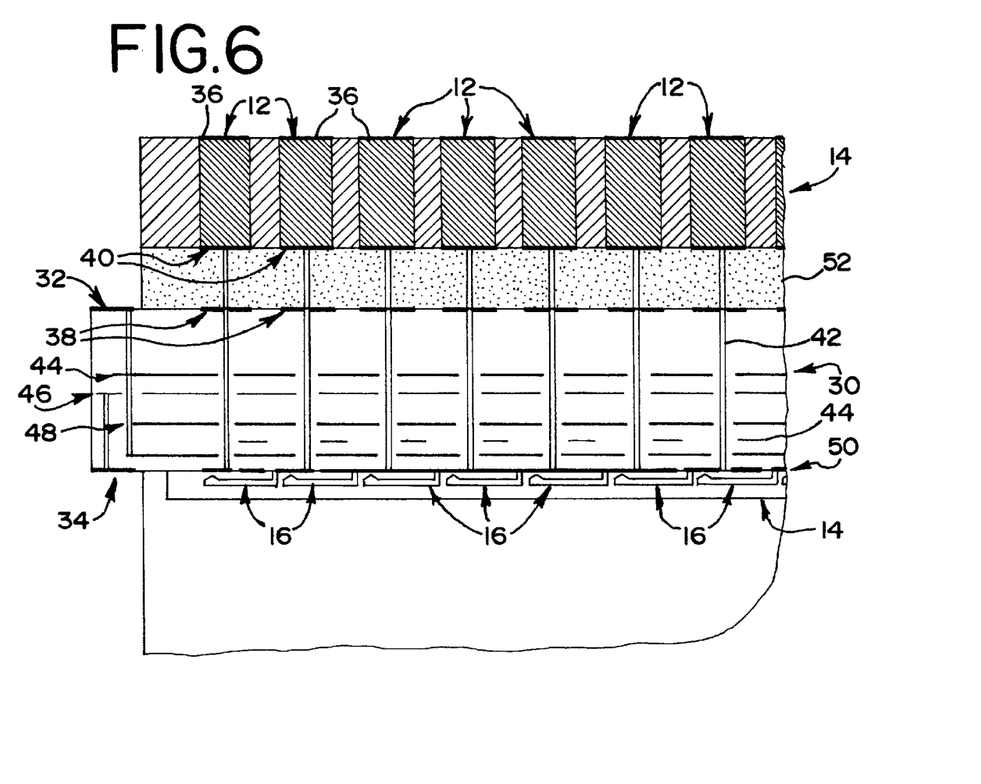
FIG. 6 is a graphical representation of an arrangement of a switching network with a transducer array.

FIG. 6 shows one embodiment of the switches 16 integrated on a substrate 30 and the substrate 30 connected with and adjacent to the two-dimensional array 14 of acoustic transducer elements 12. In this embodiment, the switches 16 comprises deflectable beam MEMS devices, but other MEMS or transistor switches may be used. The substrate 30 comprises a silicon chip, other semiconductor material, or other MEMS substrate. The substrate 30 is a same size, slightly larger, larger or smaller in one or both of the azimuth and elevation dimensions than the array 14. For example, the substrate 30 is slightly larger than the array 14 in both azimuth and elevation dimensions to allow placement of ground and signal pads 32, 34 for connection to other devices. The ground and signal pads 32, 34 allow control of operation of the switches 16 and/or use of the elements 12. For example, the ground pad 32 connects with the top electrode 36 of each element 12 for grounding the elements 12. The control circuitry for the MEMS switches 16 may be located with the MEMS switches 16 in the same substrate 30. A flex circuit bonded to the signal pads 34 interfaces the elements 12 with the cable or system channel 18 through the switches 16. The substrate 30 also includes area contacts 38 for connecting with the signal electrodes 40 of the elements 12, thru vias 42 for electrical connections, ground planes or grounded, patterned traces 44 (e.g. patterned to allow passage of vias 42), a channel layer 46 of patterned signal traces connected to the separate system channels 18, an access layer 48 for connecting the system channels 18 or channel layer 46 with the switches 16, and the switch control layer 50. Additional, different or fewer layers in the same or different configurations may be used. For example, the switches 16 are formed on the same wafer with a cMUT two-dimensional acoustic array 14 with the switches 16 either on the same surface as the cMUT's (e.g. membrane switches), in the bulk of the material as semiconductor switches, or on the backside of the cMUT wafer. The substrate 30 is formed using now known or later developed semiconductor or MEMS manufacturing techniques, such as CMOS techniques.

In one embodiment, the substrate 30 is bonded to the array 14 with a z-axis conductive backing 52. The conductive backing 52 comprises an acoustically absorbing and electrically insulating material with vias or wires for connecting the electrodes 40 to the contacts 38. Alternatively, the conductive backing 52 comprises an anisotropic material, such as a material with vertically aligned conductors for electrical connection. If acoustic reflections from the back of the substrate 30 can be controlled or minimized without the conductive backing 52, the substrate 30 may be directly flip chip bonded to the back of the acoustic array 14.

Figure 7:
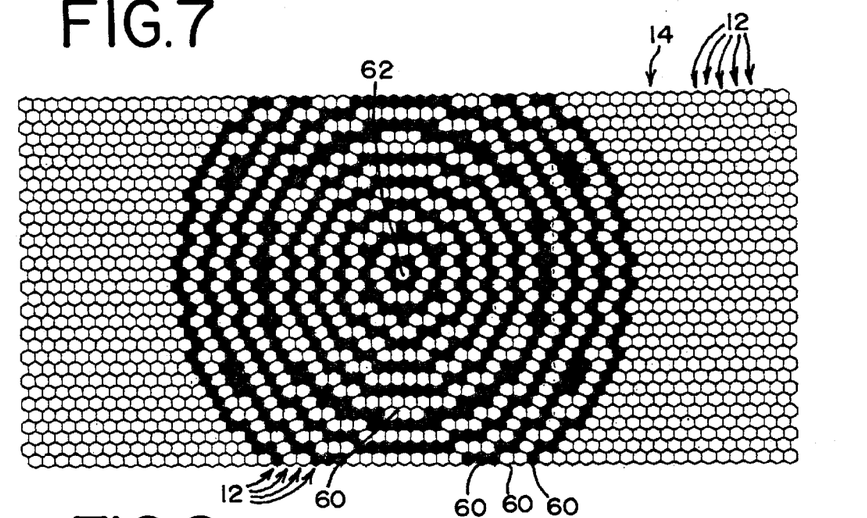
FIGS. 7–9 are three different embodiments showing possible macro element configurations.
Figure 8:
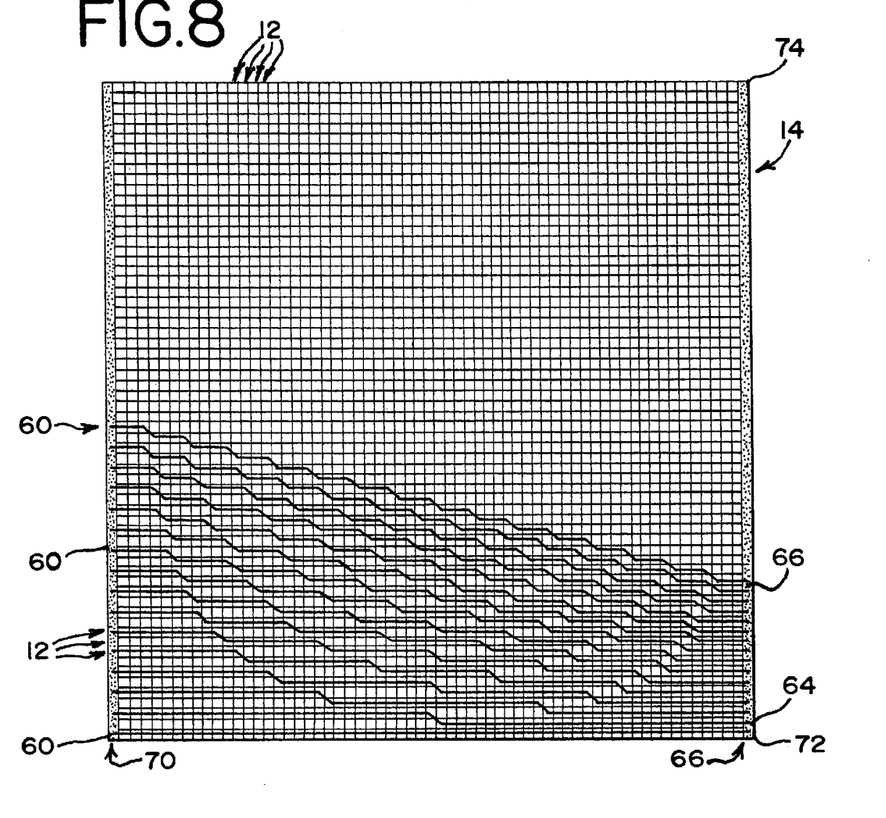

FIGS. 7–9 show various configurations of macro elements 60 for scanning within a three dimensional volume. Each macro element 60 is connected with a system channel 18, such as a receive system channel (e.g. receive beamformer channel) or a transmit system channel (e.g. transmit beamformer channel). The macro elements 60 are configured for forming a transmit or receive beam at a normal angle or an angle other than normal to the two-dimensional array 14 of elements 12 using the macro elements 60 and the system channels 18. The macro element configuration defines the beam position and/or scanning plane. For example, FIG. 7 shows one configuration of macro elements 60 for forming a beam normal to the array 14 at the center of the array 14. FIGS. 8 and 9 show possible configurations of macro elements 60 in phased arrays for forming a plurality of beams at angles different than and including the normal to the array 14. The beams are sequentially formed within the scanning plane designated by the configuration of the macro elements 60.

FIG. 7 shows one embodiment of a macro element configuration for forming beams normal to the array 14. The macro elements 60 are configured as an annular array. U.S. Pat. No. 5,563,346, the disclosure of which is incorporated herein by reference, describes use of a two-dimensional array with interconnection of elements. If the rings are split into two sections each section opposite the other across the center of the annulus, this configuration may also allow limited beam steering in the direction orthogonal to the split for Doppler applications In the example embodiment of FIG. 7, a 192×96 element 12 hexagonal grid two-dimensional array 14 with a pitch of 200 $\mu$m provides a two-dimensional aperture of 38.4 mm×16.6 mm. This grid pitch is one wavelength, $\lambda$, at 7.5 MHz. Other sizes, pitches, grids and number of elements 12 may be used. To connect adjacent elements 12 together, three switches 16 (FIG. 5) for each element 12 allow connection to any of the three adjacent elements 12 in the 30°, 90°, and 150° directions (0°=East, 90°=North). The switches 16 are opened or closed to interconnect groups of adjacent elements 12 into macro elements 60 of annular rings around a central disk 62. The annular rings of macro elements 60 correspond to elements 12 with a same or similar delay for transmitting or receiving along the beam normal to the array 14 at the central disk 62.

By reconfiguring the macro elements 60, the beam position is electronically translated. For example, the annular rings of macro elements 60 are translated by forming macro elements 60 centered around a different central disk 62. By translating to different positions within the aperture of the array 14, the three-dimensional volume is scanned.

In one embodiment, the system channels 18 are switchably connected to the macro elements 60 by assigning one system channel 18 for each macro element 60. The switches 16 are configured in two layers or groupings, one for interconnecting the elements 12 to other elements 12 and one for connecting each macro element 60 to the system channels 18. The system channel switch 16 for each element 12 may connect that element 12 to system channels 18 arranged as a zig-zag column with all of the elements 12 in the column having a system switch 16 allowing connection to the same system channel 18. For example, the element 12 of the central disk 62 connects to one system channel 18 via a system channel switch 16. Proceeding horizontally, at 0° or at 180°, each adjacent element 12 is connected via a system channel switch 16 to the next system channel 18. The system channels 18 connect with a row of elements 12 through the center of the annuli for a given configuration, all other system channel switches 16 are open. With a minimum central disk diameter and a minimum ring width of one element 12, aperture diameters larger than one hundred ninety-two elements 12 can be supported with no constraints on beam placement. If the central disk or minimum ring widths are larger than one element 12, larger aperture diameters can be supported. The number of switches 16 for the configuration described above is 4 switches 16 per element 12. A total of 4*96*192=73,728 switches 16 are provided for this configuration. This configuration also supports 1D, 1.25D, 1.5D or 1.75 phased array beamforming. Other switch configurations for interconnecting elements 12 and system channels 18 may be used, such as including more or fewer switches.

FIGS. 8 and 9 show configurations of macro elements 60 for one dimensional or 1.75 dimensional phased array operation. Beams at various angles, including normal and other than normal, to the array 14 are provided in one of various possible scan planes defined by the configuration of macro elements 60. A plurality of macro elements 60 are configured parallel to each other across the array 14 to form the phased array. The macro elements 60 are formed as substantially straight lines in at least two dimensions on the two-dimensional array 14. Since the array 14 may be concave or convex, the substantially straight is in the azimuth and elevation dimensions. Alternatively, the macro elements 60 are straight in three dimensions, such as for a flat two-dimensional array 14. The macro elements 60 extend across the face of the two-dimensional transducer array 14 from one edge to another edge.

FIG. 8 shows one embodiment of a two-dimensional array 14 with macro elements 60 reconfigurable as an electronically rotatable one dimensional phased array. In this example, a 64×64 element rectangular grid two-dimensional array 14 with a pitch of 300 μm has a 19.2 mm×19.2 mm aperture. This two-dimensional grid pitch is λ/2 at 2.5 MHz. Different grids, sizes, pitches and number of elements may be used. For grouping the elements 12 into macro elements 60, four switches 16 are provided for each element 12. The elements 12 may connect to any of the four adjacent elements in the 0°, 45°, 90°, and 135° directions (FIG. 4). The switches 16 are opened or closed to connect groups of up to 64 adjacent elements 12 into substantially straight line segments or macro elements 60. Each macro element 60 is up to 64 elements long by 1 element wide, but wider, longer or shorter macro elements 60 may be used.

A plurality of parallel macro elements 60 are formed across the array 14, forming a one-dimensional phased array defining a scanning plane in the direction perpendicular to the parallel macro elements 60. For example, separate, parallel macro elements 60 are repeated at a horizontal angle (see horizontal macro element 64). The resulting scanning plane extends at a normal angle from the array 14 in a vertical alignment. A single selected macro element 60 is repeated over the two-dimensional array 14 at any point in time, forming a two-dimensional imaging plane which is orthogonal to the long axis of the phased array of macro elements 60.

FIG. 8 shows non-parallel macro elements 60 extending from a horizontal macro element 64 to an about 14° macro element 66. These different elements represent different macro element configurations for defining scan planes at different angles relative to the two-dimensional array 14, such as for scanning in different planes and then electronically rotating the scan plane for three-dimensional imaging. The different configurations include a plurality of substantially straight, parallel macro elements 60 at different angles, respectively. For example, a plurality of beams are formed using the configuration based on the angle of a plurality of macro elements like macro element 64 at zero degrees within the array 14 (i.e. a first two-dimensional scan plane is scanned). A plurality of beams are later formed using the configuration based on the angle of a plurality of macro elements like macro element 66 at about 14° within the array 14 (i.e. a second, different two-dimensional scan plane is scanned). One element 12 may be originally connected to a second element 12 for scanning in one scan plane, then reconfigured to not connect to the second element 12 but to connect to a third element 12 for scanning in a different scan plane. The process repeats for different configurations, effectively rotating the two-dimensional scan plane within the three-dimensional volume.

By changing the pattern of closed switches 16, the system 10 controls the direction the one-dimensional macro elements 60 are pointed relative to the array 14. For a 64×64 element array, there may be 252 pointing directions between 0° and 180°, so the minimum angle between pointing directions is <1°. FIG. 8 shows sixteen of the macro elements and associated angles of zero degrees to about 14°. Sixty four macro element configurations are provided between 0° to 45°, and sixty four macro element configurations are provided between 135° to 180°.

For the embodiment of FIG. 8, the system channels 18 connect to the elements 12 on the right and left edges or columns 68 and 70 for macro element angles from −45° to +45°. For angles from +45° and +135°, the switches 16 around the periphery connecting to system channels 18 change state to connect the system channels 18 to the edge elements 12 on the top and bottom edges or rows 72 and 74. The macro elements 60 configured as a one-dimensional array connect with the edges of the two-dimensional array aperture. In one embodiment, the system channels 18 are switched between connection to the set of right/left edges, and the set of top/bottom edges using an additional set of switches 16, requiring one additional switch 16 for each element 12 around the periphery. One system channel 18 is selectably switched between one element 12 on one edge and another element 12 on a different edge. These switches 12 change switch state as the image plane angle is moved across the diagonals. In other embodiments, different elements 12 are switchably connectable with the system channels 18.

Focusing in the direction perpendicular to the scanning plane (elevation relative to the macro elements 60) may be implemented with an acoustic array with spherical concave curvature or a mechanical lens. This imparts an effective concave curvature in both the elevation plane as well as the imaging plane (azimuth relative to the macro elements 60). The effective curvature in the imaging plane is counteracted or accounted for using beamformer delays.

FIG. 9 shows one embodiment of the two-dimensional array 14 with macro elements 60 reconfigurable as an electronically rotatable 1.75D phased array. The macro elements 60 are configured as substantially straight in at least two dimensions in multiple rows 80 of macro elements. The thick black lines at +30° show the boundaries of the rows 80. Within each row 80, a plurality of parallel macro elements 60 are provided. Two or more, such as three, four or five, rows 80 are provided. For example, FIG. 9 shows a portion of a 50×44 element hexagonal grid two-dimensional array 14 with a pitch of 187 μm, providing a 9.4 mm×9.5 mm aperture. This pitch is one half a wavelength, λ/2, at 4 MHz. In the top row 80 of the array 14, macro elements 60 are shown interconnected for ten different scanning planes. The different macro element patterns 60 shown in the top row 80 are used at different times. The ten scanning planes correspond to angles from 0° to 60° in approximate 6° steps relative to the two-dimensional array 14. For a given scanning plane or time, one of the interconnection patterns or macro elements, such as macro element 82, shown in the top row 80 is repeated along the upper row 80, providing a plurality of substantially straight, parallel macro elements 60 in the row 80. The same or different interconnection pattern is repeated in the other rows 80, as shown in the middle and lower rows 80 of FIG. 9. The scanning plane defined by the repeated pattern of macro element 82 in the three rows 80 is designated by the arrow 84 and is at 18° relative to the array 14.

For electronically rotating the multi-dimensional array and scanning in a different scan plane, the macro elements 60 are re-interconnected with the macro elements 60 at different angles to the array 14. For example, the rows 80 are kept at a same angle relative to the array 14, but the angle of the macro elements 60 is changed by reconfiguring the interconnection of the elements 12. The rows 80 are the same for scanning planes at 0° to 60°. For scanning planes at angles of 60° to 120°, the rows rotate by 60°. For scanning planes at angles of 120° to 180°, the rows rotate by another 60°. Smaller adjustment of the scanning plane angle is achieved by using different beamforming delays between rows.

In one embodiment, an ultrasound system has 200 system channels 18 for use with the array 14 of FIG. 9 as a 1.75D array. Four rows 80 by 50 columns or macro elements 60, five rows 80 by 40 columns or macro elements 60, or other numbers of macro elements 60 or rows may used. With 2,200 elements 12 and 200 system channels 18, each 1.75D macro element 60 is eleven elements 12 long, but other numbers of elements may be interconnected to form a macro element 60. Three switches 16 are provided for each element 12 (FIG. 5), allowing connection of the element 12 to three adjacent elements 12 at 30°, 90°, and 120°. Switching the macro element pattern allows the 1.75D elements to be configured in 30 discrete angles between 0° and 180°. Additional scanning planes may be obtained by small beamforming delays between rows 18 implemented in the system channels 18.

In addition to the switches 16 for interconnecting the elements 12, switches 16 connect the macro elements 60 with system channels 18. Each system channel 18 is switched between one of three elements 12 located at the centers, edges or other locations of the possible 1.75D rows. For example, the centers of the possible 1.75D rows 80 lie along one of the three principal directions (30°, 90°, and 120°) shown in FIG. 9 as shaded elements 86, 88 and 90. For any given row configuration, three switches 16 are provided for each system channel 18. The three switches 16 connect a given system channel 18 to one of three elements 12, one element 12 for each row angle. Different system channels 18 are connectable with different elements 12 along the center of each row 80. As a result, the system channels 18 are switched to the elements 12 along the center line 90 at 30°, connecting the macro elements 60 to the system channels 18 at the center of each macro element 60. To cover scanning plane angles of 60° to 120°, the system channels 18 are switched to the elements 12 along the center lines 86 at 90° (vertical center lines). To cover scanning plane angles of 120° to 180°, the system channels 18 are switched to the elements 12 along the center lines 88 at 150°. This example embodiment uses 3*(2200+200)=7,200 switches 16. Other embodiments using more or fewer angles, macro elements, elements, rows, switches or other array characteristics may be used. Different pitches, sizes or other array characteristics may also be used.

Focusing in the direction perpendicular to the scanning plane (elevation relative to the macro elements 60) may be implemented with an acoustic array with spherical concave curvature or a mechanical lens. This imparts an effective concave curvature in the imaging plane (azimuth relative to the macro elements 60). The effective curvature in the imaging plane is counteracted or accounted for using beamformer delays.

In one embodiment, the elements 12 are interconnected as a function of aberration correction. The macro element is formed based on time delays introduced by aberrations in the tissue being imaged. As a result, the curves or substantially straight lines of elements representing a same delay are altered to account for aberration correction. One or more elements 12 are connected to a different macro element due to the correction. For example, the macro elements may have a zig-zag or varying pattern due to aberration correction. The macro elements may be irregularly shaped and vary in shape or configuration from one element to another.

Other embodiments configure the macro elements for electronic translation as an alternative or in addition to rotation of the scanning plane. For example, a first scan plane corresponds to macro elements extending only partially along an elevation extent of the array. The angle of the macro elements determines the elevation extent of the array. Additional scan planes are formed by translating the elevation aperture or position of the macro elements along the elevation extent of the array. Translation of the scanning plane may extend the cross-sectional area of the imaged volume to the skinline or transducer surface and may be useful for measuring tissue aberration to determine delay based adjustments of the macro elements.

While the invention has been described above by reference to various embodiments, it should be understood that many changes and modifications can be made without departing from the scope of the invention. For example, combinations of curved, irregularly shaped and substantially straight macro elements may be used at a same time or as part of a same configuration; macro elements at different angles or not parallel to each other may be used as part of the same configuration; macro elements of different sizes may be used as a function of focusing depth or as part of a same configuration; fewer than all of the elements 12 may be interconnected as macro elements or other combinations of elements to form any of various annular or phased arrays; and different combinations of type of macro element array with different element sampling and grid patterns may be used. The above embodiments are examples.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for scanning within a three dimensional volume, the method comprising:
   (a) switchably interconnecting at least first and second elements of a two-dimensional array of elements and a system channel, the at least first and second elements comprising a first macro element;
   (b) forming a first beam at an angle other than normal to the two-dimensional array of elements using at least the first macro element and the system channel, the first beam within a first plane responsive to the first macro element; and
   (c) switchably interconnecting the first element with a third element of the two-dimensional array of elements, the first and third element comprising a second macro element corresponding to a second plane at a non-orthogonal angle to the first plane.

2. The method of claim 1 wherein (a) and (c) are repeated for a plurality of planes within the three dimensional volume, each plane associated with different macro element configurations of the two dimensional array of elements, and wherein (b) is repeated a plurality of times for each plane.

3. The method of claim 2 wherein (a) and (c) comprise electronically rotating scanning planes and (b) comprises two-dimensional scanning of each of the scanning planes.

4. The method of claim 1 wherein (a) comprises interconnecting the at least first and second elements wherein the first and second elements are adjacent elements in one of: a triangular, a rectangular and a hexagonal sampling grid.

5. The method of claim 4 wherein (a) comprises interconnecting with less than five switches for each element.

6. The method of claim 1 wherein (a) and (c) comprise forming the first and second macro elements as substantially straight lines on the two-dimensional array of elements.

7. The method of claim 6 wherein (a) comprises interconnecting the at least first and second elements of a phased array.

8. The method of claim 1 wherein (a) comprises forming the first macro element and a first plurality of substantially parallel macro elements and (c) comprises forming the second macro element and a second plurality of substantially parallel macro elements, the first plurality of substantially parallel macro elements at a different angle on the two-dimensional array of elements than the second plurality of substantially parallel macro elements.

9. The method of claim 1 wherein (a) comprises forming a first plurality of first rows of macro elements, each first row of macro elements having a first plurality of macro elements.

10. The method of claim 9 wherein (c) comprises forming a second plurality of second rows of macro elements, each second row of macro elements having a second plurality of substantially parallel macro elements, but the substantially parallel macro elements of (c) at a first different angle than the substantially parallel macro elements of (a).

11. The method of claim 10 wherein (a) and (c) comprise forming the first rows at a different angle than the second rows.

12. The method of claim 1 wherein (a) comprises forming one of a: 1.5D and 1.75D configuration of macro elements.

13. The method of claim 1 wherein (a) and (c) comprise switching the at least first and second elements with switches connected in parallel to the system channel.

14. The method of claim 1 wherein (a) and (c) comprise switching the at least first and second elements with switches connected in series to the system channel.

15. The method of claim 1 wherein (a) and (c) comprise switching with microelectromechanical switches connected adjacent to the two-dimensional array of elements.

16. The method of claim 1 wherein (a) comprises forming the first macro element and a plurality of macro elements with more than one switch per system channel.

17. A method for scanning within a three dimensional volume, the method comprising:
(a) switchably interconnecting at least first and second elements of a two-dimensional phased array of elements and a system channel, the at least first and second elements comprising a first macro element, the first macro element substantially straight in at least two dimensions;
(b) forming at least a first beam using at least the first macro element and the system channel; and
(c) switchably interconnecting the first element with a third element of the two-dimensional array of elements, the first and third element comprising a second macro element corresponding to a second plane different than the first plane; and
(d) switchably interconnecting the first element with a fourth element of the two-dimensional array of elements, the first and fourth element comprising a third macro element corresponding to a third plane different than the first and second planes.

18. The method of claim 17 wherein (a) comprises forming the first macro element and a first plurality of substantially parallel macro elements and (c) comprises forming the second macro element and a second plurality of substantially parallel macro elements, the first plurality of substantially parallel macro elements at a different angle on the two-dimensional array of elements than the second plurality of substantially parallel macro elements.

19. The method of claim 17 wherein (a) comprises forming a first plurality of first rows of macro elements, each first row of macro elements having a first plurality of macro elements, wherein (c) comprises forming a second plurality of second rows of macro elements, each second row of macro elements having a second plurality of substantially parallel macro elements, but the substantially parallel macro elements of (c) at a first different angle than the substantially parallel macro elements of (a).

20. A method for scanning within a three dimensional volume, the method comprising:
(a) switchably interconnecting a plurality of elements of a two-dimensional phased array into a plurality of macro elements, each macro element comprising at least two interconnected elements, the plurality of macro elements configured in a plurality of rows, each row comprising a plurality of macro elements, the macro elements extending between row boundaries, a row boundary and an edge of the array or two edges of the array;
(b) connecting each macro element with a system channel; and
(c) forming at least a first beam using the macro elements and the system channels.

21. The method of claim 20 wherein (a) comprises configuring a plurality of substantially parallel macro elements within each of the plurality of rows.

22. The method of claim 20 further comprising:
(d) re-interconnecting the plurality of elements into a different plurality of macro elements configured as one of a 1.5D and 1.75D array of macro elements, the macro elements of (d) being at a different angle on the two-dimensional array than the macro elements of (a).

23. The method of claim 20 wherein (c) comprises forming the first beam at an angle other than normal to the two-dimensional array.

24. A two-dimensional transducer array system for ultrasonically scanning a three dimensional volume, the system comprising:
a two-dimensional array of acoustic transducer elements;
a plurality of switches operable to interconnect the elements into a plurality of macro elements, each macro element comprising at least two elements in a substantially straight line in at least two dimensions; and
a plurality of system channels operable to be connected with respective macro elements;
wherein at least two switches for forming the macro element connect with each system channel.

25. The system of claim 24 wherein the switches comprise microelectromechanical switches.

26. The system of claim 24 wherein the switches are operable to connect with the system channels in a parallel arrangement.

27. The system of claim 24 wherein the switches are operable to connect with the system channels in a series arrangement.

28. The system of claim 24 wherein the switches are integrated on a substrate, the substrate connected with and adjacent to the two-dimensional array of acoustic transducer elements.

29. The system of claim 24 wherein at least an average of more than one switch is provided for each element.

30. The system of claim 24 wherein the plurality of switches are operable to re-interconnect the elements into different macro element configurations, the different macro element configurations corresponding to different angles on the two-dimensional array.

31. The system of claim 24 wherein the plurality of macro elements are configured for beamforming along a beam line extending at a non-normal angle to the two-dimensional array.

32. The system of claim 24 wherein the plurality of macro elements are configured in at least two parallel rows, each row comprising a plurality of substantially parallel macro elements.

33. A two-dimensional transducer array system for ultrasonically scanning a three dimensional volume, the system comprising:

a two-dimensional array of acoustic transducer elements;

a plurality of switches operable to interconnect the elements into at least first and second different configurations of a plurality of macro elements, each macro element comprising at least two elements in a substantially straight line in at least two dimensions, the first configuration having macro elements at a different, non-orthogonal angle on the two-dimensional array than the second configuration; and a plurality of system channels operable to be connected with respective macro elements.

34. The method of claim 33 wherein at least two switches are provided for each system channel.

35. The system of claim 33 wherein the plurality of macro elements are configured for beamforming along a beam line extending at a non-normal angle to the two-dimensional array.

36. The system of claim 33 wherein the first configuration comprises macro elements configured in at least two parallel rows, each row comprising a plurality of substantially parallel macro elements.

37. The method of claim 1 wherein (c) comprises forming the second and additional macro elements with different patterns as a function of aberration correction.

38. The method of claim 17 wherein (a), (c) and (d) comprise translating a scan plane position, the first, second and third scan planes corresponding to the translated scan plane position.

39. The system of claim 24 wherein the elements have one of triangular, rectangular or hexagonal shapes.

* * * * *